United States Patent [19]

Desmurs et al.

[11] Patent Number: 5,189,218
[45] Date of Patent: Feb. 23, 1993

[54] PREPARATION OF N-PHENYLBENZOQUINONE-IMINE AND CONVERTING SAME INTO P-PHENYLENEDIAMINES

[75] Inventors: Jean-Roger Desmurs, St Symphorien D'Ozon; Hubert Kempf, Mulhouse; Serge Ratton, Saint Germain en Laye; Dominique Stephan, Venissieux, all of France

[73] Assignee: Rhone-Poulenc Chimie, Courbevoie, France

[21] Appl. No.: 668,637

[22] Filed: Mar. 13, 1991

[30] Foreign Application Priority Data

Mar. 13, 1990 [FR] France .................... 90 03447

[51] Int. Cl.$^5$ ............................ C07C 249/02
[52] U.S. Cl. ..................... 564/272; 564/271; 564/434
[58] Field of Search ................ 564/272, 271

[56] References Cited

U.S. PATENT DOCUMENTS

| 3,867,094 | 2/1975 | Kalopissis et al. | 8/10 |
| 3,894,837 | 7/1975 | Kalopissis et al. | 8/10 |
| 3,963,764 | 6/1976 | Kalopissis et al. | 260/396 M |
| 3,984,402 | 10/1976 | Kalopissis et al. | 260/244 R |
| 4,045,170 | 8/1977 | Kalopissis et al. | 8/11 |
| 4,968,843 | 11/1990 | Cottman | 564/397 |

FOREIGN PATENT DOCUMENTS

| 752381 | 12/1970 | Belgium . |
| 2331878 | 1/1974 | Fed. Rep. of Germany . |
| 2121101 | 8/1972 | France . |
| 1382206 | 1/1975 | United Kingdom . |

OTHER PUBLICATIONS

Denisov et al. Izv. Akad. Nauk. SSSR, Ser. Khim., (10) 2217-23 (1988) (Abstract).
Albright, "Sulfoxarium Salt as Reagents for the Oxidation of Primary & Secondary Alcohols to Carbonyl Compounds", J. Org. Chem., vol. 39, No. 13, 1974 pp. 1977-1979.
Research Disclosure 2244 No. 173 (1978/09) "Process of Preparing Polyaniline Amines" (Gautier).

Primary Examiner—Richard L. Raymond
Assistant Examiner—Brian M. Burn
Attorney, Agent, or Firm—Burns, Doane, Swecker & Mathis

[57] ABSTRACT

N-phenylbenzoquinone-imine is prepared by oxidizing N-(4-hydroxyphenyl)aniline in a liquid, at least partially organic reaction medium, in the presence of a basic compound and, advantageously, a catalytically effective amount of at least one manganese, copper, cobalt and/or nickel compound; this imine can be reacted with an aliphatic or cycloaliphatic amine to produce an N-phenyl-N'-cycloalkyl-para-phenylene-diamine and an N-phenyl-N'-cycloalkyl-2,5-cyclohexadiene-1,4-diimine, such 1,4-diimine itself being easily reduced to the corresponding p-phenylenediamine.

18 Claims, No Drawings

PREPARATION OF N-PHENYLBENZOQUINONE-IMINE AND CONVERTING SAME INTO P-PHENYLENEDIAMINES

BACKGROUND OF THE INVENTION

1. Field of the Invention

The present invention relates to the preparation of N-phenylbenzoquinone-imine by oxidation of N-(4-hydroxyphenyl)aniline.

This invention also relates to the reaction of the N-phenylbenzoquinone-imine thus obtained with an aliphatic or cycloaliphatic amine, to prepare an N-phenyl-N'-cycloalkylparaphenylenediamine and an N-phenyl-N'-cycloalkyl-2,5-cyclohexadiene-1,4-diimine (this latter compound is itself easily reduced to the corresponding N-phenyl-N'-cycloalkylpara-phenylenediamine).

2. Description of the Prior Art

The N-phenyl-N'-alkyl-paraphenylenediamines are currently prepared, in particular, by reduction, then by alkylation of para-nitrodiphenylamine.

Thus, U.S. Pat. No. 4,463,191 describes a process for the reduction/alkylation of para-nitrodiphenylamine, with ketones or aldehydes, in the presence of palladium-/anthranilic acid complex fixed onto an unbranched polymer, and in the presence of a sulfonated resin. The catalyst is required to be prepared in several stages.

SUMMARY OF THE INVENTION

A major object of the present invention is the provision of a novel process for the preparation of N-phenylbenzoquinone-imine and to the conversion of such imine into the N-phenyl-N'-cycloalkyl-paraphenylenediamines.

Briefly, the present invention features the oxidation of N-(4-hydroxyphenyl)aniline into N-phenylbenzoquinone-imine, such oxidation being carried out in a liquid, at least partly organic reaction medium, in the presence of a basic compound.

DETAILED DESCRIPTION OF THE PREFERRED EMBODIMENTS OF THE INVENTION

More particularly according to the present invention, the subject oxidation process is advantageously carried out in the presence of a catalytically effective amount of at least one metal compound selected from among the manganese, copper, cobalt and nickel compounds.

In a first embodiment of the invention, the liquid medium in which the oxidation reaction is carried out is completely organic, and the basic compound is a tertiary amine.

Such tertiary amine characteristically has the general formula (I):

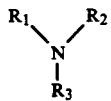

wherein $R_1$ and $R_2$, which may be identical or different, are each a linear or branched chain alkyl radical having 1 to 12 carbon atoms or a phenyl radical, and $R_3$ is a linear or branched chain alkyl radical having 1 to 12 carbon atoms, a linear or branched chain alkenyl radical having 2 to 12 carbon atoms, a phenyl radical, a substituted phenyl radical bearing one or two linear or branched chain alkyl radicals having 1 to 4 carbon atoms, a cyclohexyl or cyclopentyl radical, or a benzyl or phenethyl radical.

Among the tertiary amines of formula (I), the non-quaternizable trialkylamines are particularly preferred, in which $R_1$, $R_2$ and $R_3$ are linear or branched chain alkyl radicals having 1 to 12 carbon atoms.

Exemplary tertiary amines of formula (I) include diisopropylethylamine, dicyclohexylethylamine, di(1-methylpropyl)ethylamine, n-propyldiisopropylamine, diisobutylethylamine, allyldiisopropylamine, allyl-diisobutylamine and diphenylethylamine.

The amount of tertiary amine present, in moles, is advantageously at least 1% of the molar quantity of N-(4-hydroxyphenyl)aniline introduced.

Preferably, it ranges from 1% to 1,000% of the molar quantity of N-(4-hydroxypheny))aniline, and more preferably from 50% to 300%.

The tertiary amine can itself constitute the organic solvent of the reaction medium according to the present invention.

It is also possible to carry out the reaction in an inert organic solvent which differs from the tertiary amine.

Exemplary such organic solvents include alcohols, such as, for example, methanol, ethanol, isopropyl alcohol, trifluoroethanol, cyclohexanol; ethers, such as diisopropylether, methyltertbutylether, tetrahydrofuran, dioxane; ketones such as acetone, methylisobutylketone, cyclohexanone; nitriles, such as acetonitrile; N-alkylatedamides, such as dimethylformamide, dimethylacetamide, N-methylpyrrolidone; aliphatic or chlorinated aliphatic hydrocarbons, such as hexane, dichloromethane, dichloroethane, trichloromethane (or chloroform); aromatic or chlorinated aromatic hydrocarbons, such as toluene, xylenes, chlorobenzene, dichlorobenzenes; cycloaliphatic hydrocarbons, such as cyclohexane; esters, such as ethyl acetate; sulfoxides, such as dimethylsulfoxide.

Among these solvents, the alcohols are particularly well suited, in particular methanol, ethanol, isopropanol and trifluoromethylethanol.

In a second embodiment of the invention, the liquid medium in which the oxidation reaction is carried out is hydro organic, and the basic compound is an alkali metal hydroxide.

The organic solvent which, together with water, constitutes such liquid medium is typically a solvent which is immiscible with water, selected from among the alcohols, ethers, ketones, nitriles, aliphatic and chlorinated aliphatic hydrocarbons, aromatic hydrocarbons and chlorinated aromatic hydrocarbons, and cycloaliphatic hydrocarbons.

The preferred such solvents are the aliphatic hydrocarbons or chlorinated aliphatic hydrocarbons, such as hexane, dichloromethane, chloroform, dichloroethane, trichloroethane; aromatic hydrocarbons or chlorinated aromatic hydrocarbons, such as toluene, xylenes, chlorobenzene, dichlorobenzenes; cycloaliphatic hydrocarbons such as cyclohexane. These are preferred because they at least partially dissolve the N-phenylbenzoquinone-imine formed.

Among the alkali metal hydroxides, sodium hydroxide is usually preferred because it is economical.

Typically, the amount of alkali metal hydroxide is such that the molar ratio alkali metal hydroxide/N-(4-hydroxyphenyl)aniline ranges from 5% to 500%, preferably from 10% to 100%.

The volume ratio water/organic solvent advantageously ranges from 0.01 to 100 and preferably from 0.1 to 10.

The manganese, copper, cobalt and nickel compounds indicated above are advantageously salts of manganese, copper, cobalt or nickel with mono- or polyfunctional carboxylic acids, such as, for example, acetic, propionic, succinic, benzoic acids, halocarboxylic acids, such as chloroacetic and fluoroacetic acids; halosulfonic acids, such as trifluoromethanesulfonic acid; inorganic acids, such as hydrohalide acids, e.g., hydrochloric acid, hydrobromic acid, hydrofluoric acid or hydriodic acid; sulfuric acid; nitric acid; perchloric acid; phosphoric acids; carbonic acid and manganese, copper, cobalt or nickel oxides or hydroxides.

The oxidation can be carried out using oxygen or a gas containing oxygen, such as air or a mixture of oxygen/nitrogen, for example.

The oxygen or oxygen-containing gas can be used at atmospheric pressure, such as, for example, by bubbling it into the reaction mixture or simply by circulating it in the reactor where the oxidation reaction is carried out, or at increased pressure.

Advantageously, the partial pressure of the oxygen ranges from 0.02 MPa (0.2 bar) to 2 MPa (20 bars).

The metal compound of manganese, copper, cobalt or nickel serves as a catalyst and typically is present in an amount ranging from 0.1% to 100% in moles, relative to the N-(4-hydroxyphenyl)aniline.

The molar ratio of manganese, copper, cobalt or nickel compound/N-(4-hydroxyphenyl)aniline preferably ranges from 2% to 20%.

In the first embodiment of the process of the invention, using a reaction medium which is completely organic and a tertiary amine, the compound of manganese, copper, cobalt or nickel can itself be the oxidizing agent.

In this case, the molar ratio of manganese, copper, cobalt or nickel compound/N-(4-hydroxyphenyl)aniline thus ranges from 0.9 to 3, preferably from 1.0 to 1.5.

In the second embodiment of the process of the invention, using a hydro/organic reaction medium and an inorganic base, the oxidizing agent can also be a conventional chemical oxidizing agent, such as, for example, hydrogen peroxide, in an amount which is substantially at least stoichiometric with respect to the N-(4-hydroxyphenyl)aniline.

The temperature at which the process of the invention is carried out can vary over a very wide range.

The process is advantageously carried out at a temperature ranging from 5° C. to 120° C., preferably from 10° C. to 80° C.

The N-phenylbenzoquinone-imine produced is a useful intermediate compound from which is prepared the N-phenyl-N'-cycloalkyl-paraphenylenediamines and the corresponding N-phenyl-N'-cycloalkyl-2,5-cyclohexadiene-1,4-diimines, by condensation with a primary aliphatic or cycloaliphatic amine.

The imine can be isolated using conventional techniques.

Thus, the present invention also features a process for the preparation of an N-phenyl-N'-cycloalkylparaphenylenediamine of the general formula (II):

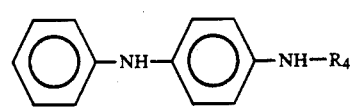

and a process for the preparation of an N-phenyl-N'-cycloalkyl-2,5-cyclohexadiene-1,4-diimine of the general formula (III):

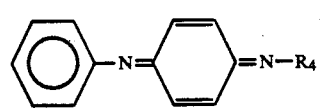

wherein $R_4$ is a linear or branched chain alkyl radical having 1 to 12 carbon atoms, or a cycloalkyl radical having 5 to 8 carbon atoms, comprising reacting N-phenylbenzoquinone-imine, in a liquid reaction medium, with an amine of the general formula (IV):

$$R_4—NH_2 \quad (IV)$$

wherein $R_4$ is as defined above.

Exemplary amines of formula (IV) include 1,3-dimethylbutylamine, ethylamine, methylamine, isopropylamine, n-propylamine, 2-methylpropylamine, n-butylamine, 1-methylbutylamine, 1,2-dimethylpropylamine, 1,1-dimethylpropylamine, 2-methylbutylamine, 3-methylbutylamine, 1-ethylpropylamine, 1,1-dimethylethylamine, pentylamine, hexylamine, 1-methylpentylamine, 2-methylpentylamine, 3-methylpentylamine, 4-methylpentylamine, 1,2-dimethylbutylamine, 1-ethylbutylamine, 2-ethylbutylamine, heptylamine and the isomers thereof, octylamine and the isomers thereof, nonylamine and the isomers thereof, decylamine and the isomers thereof, cyclopentylamine, cyclohexylamine, methylcyclohexylamines and cyclooctylamine.

1,3-Dimethylbutylamine is particularly preferred because N-phenyl-N'-(1,3-dimethylbutyl)paraphenylenediamine is produced therefrom, a useful antizone agent (antioxidant) for natural or synthetic rubbers.

The molar ratio of the amine of formula (IV)/N-phenylbenzoquinone-imine advantageously ranges from 0.9 to 6.

This ratio preferably ranges from 0.9 to 1.3.

The liquid in which the reaction is carried out can be any at least partial solvent for the N-phenylbenzoquinoneimine and the amine of formula (IV), to the extent that such solvent does not react with the reagents under the operating conditions of the reaction.

Particularly exemplary such solvents include the alcohols, such as, for example, methanol, ethanol, isopropyl alcohol, trifluoroethanol, cyclohexanol; ethers, such as diisopropylether, methyl-tertbutylether, tetrahydrofuran, dioxane; ketones, such as acetone, methylisobutylketone, cyclohexanone; nitriles, such as acetonitrile; N-alkylatedamides, such as dimethylformamide, dimethylacetamide, N-methylpyrrolidone; aliphatic or chlorinated aliphatic hydrocarbons, such as hexane, dichloromethane, dichloroethane, trichloromethane (or chloroform); aromatic or chlorinated aromatic hydrocarbons, such as toluene, xylenes, chlorobenzene, dichlorobenzenes; cycloaliphatic hydrocarbons, such as cyclohexane; esters such as ethyl acetate; sulfoxides, such as dimethylsulfoxide.

Among these solvents, the alcohols are particularly preferred.

The initial concentration of the N-phenylbenzoquinone-imine in the solvent can vary greatly. It typically ranges from 1% to 40% by weight in relation to the weight of the reaction mixture.

It is preferable to employ initial concentrations of N-phenylbenzoquinone-imine ranging from 4% to 25% in weight by weight of the reaction mixture.

The temperature at which the reaction between the N-phenylbenzoquinone-imine and the amine of formula (IV) is carried out typically ranges from 5° to 80° C., preferably from 10° to 60° C.

The N-phenyl-N'-cycloalkyl-2,5-cyclohexadiene-1,4-diimine which is often obtained in major amounts in the reaction of N-phenylbenzoquinone-imine with the amine of formula (IV) can easily be reduced to the corresponding N-phenyl-N'-cycloalkyl-para-phenylenediamine using any known means, e.g., hydrogenation by $H_2$ in the presence of a conventional catalyst, chemical reduction, for example using a metal hydride.

The N-phenyl-N'-cycloalkyl-paraphenylenediamine are compounds which are useful anti-ozone agents in vulcanizates based on natural rubber or a synthetic elastomer.

In order to further illustrate the present invention and the advantages thereof, the following specific examples are given, it being understood that same are intended only as illustrate and in nowise limitative.

EXAMPLES 1 TO 3 AND COMPARATIVE TESTS A, B and C

The following reagents were introduced into a 30 cm³ glass reactor:

| | |
|---|---|
| (i) N-(4-Hydroxyphenyl)aniline | 1 g (5.4 mmol) |
| (ii) Metal salt (indicated in Table I below) | 5.4 mmol |
| (iii) Methanol | 5 cm³ |
| (iv) Diisopropylethylamine | 5 mmol or 0 (comparative tests). |

The reaction mixture was agitated for 2 hours at ambient temperature (20° to 25° C).

After the metal salt had been filtered therefrom, the final reaction mixture was determined by high performance liquid chromatography (HPLC).

Table I which follows reports the results obtained. The following abbreviations are used:
RT=Rate of Transformation
YO=Yield Obtained
TR=Yield with respect to transformed reagent
HPA=N-(4-hydroxyphenyl)aniline
PQI=N-phenylbenzoquinone-imine.

TABLE I

| TESTS | Metal Salt | Diisopropyl ethylamine (mmol) | RT % HPA | YO % PQI | TR % PQI |
|---|---|---|---|---|---|
| Example 1 | Mn Cl$_2$.2H$_2$O | 5 | 70 | 10 | 15 |
| Test A | MnCl$_2$.2H$_2$O | 0 | 1.5 | 0.3 | 20 |
| Example 2 | CuSO$_4$ | 5 | 63 | 25 | 40 |
| Test B | CuSO$_4$ | 0 | 6 | 3 | 50 |
| Example 3 | CuCl | 5 | 39 | 27 | 69 |
| Test C | CuCl | 0 | 21 | 7 | 34 |

EXAMPLES 4 TO 9 AND TESTS D TO H

The following reagents were introduced into a 30 cm³ glass reactor:

| | |
|---|---|
| (i) N-(4-Hydroxyphenyl)aniline | 1 g (5.4 mmol) |
| (ii) Metal salt (type and quantity indicated in Table II below) | |
| (iii) Methanol | 5 cm³ |
| (iv) Diisopropylethylamine indicated in Table II below. | amount |

The reaction mixture was agitated for 2 hours at ambient temperature (20° to 25° C.), while air was introduced using a capillary tube.

After the metal salt had been filtered therefrom, the final reaction mixture was determined by HPLC. The results are reported in Table II.

The abbreviations used are the same as in Table I.

TABLE II

| TESTS | Metal Salt Type | Quantity (mmol) | Diisopropyl ethylamine (mmol) | RT % HPA | YO % PQI | TR % PQI |
|---|---|---|---|---|---|---|
| Example 4 | CuSO$_4$ | 0.54 | 5 | 82 | 56 | 68 |
| Test D | CuSO$_4$ | 0.54 | 0 | 3 | 1.2 | 40 |
| Example 5 | CoCl$_2$ | 0.54 | 5 | 46 | 29 | 62 |
| Test E | CoCl$_2$ | 0.54 | 0 | 2 | 0.4 | 20 |
| Example 6 | CoCl$_2$ | 0.25 | 0.5 | 28 | 25 | 89 |
| Test F | CoCl$_2$ | 0.25 | 0 | 12 | 4 | 33 |
| Example 7 | MnCl$_2$.4H$_2$O | 0.25 | 5 | 78 | 70.5 | 90 |
| Test G | MnCl$_2$.4H$_2$O | 0.25 | 0 | 1.6 | — | — |
| Example 8 | CuSO$_4$.4H$_2$O | 0.15 | 0.75 | 76 | 55 | 72 |
| Example 9 | CuSo$_4$.4H$_2$O | 0.15 | 7.5 | 91 | 82 | 90 |
| Test H | CuSo$_4$.4H$_2$O | 0.15 | 0 | 7 | 4 | 60 |

EXAMPLES 10 TO 11

The following reagents were introduced into a 30 cm³ glass reactor:

| | |
|---|---|
| (i) N-(4-Hydroxyphenyl)aniline | 1 g (5.4 mmol) |
| (ii) CuSO$_4$ | 0.54 mmol |
| (iii) Solvent (indicated in Table III) | 5 mmol |
| (iv) Diisopropylethylamine | 5 mmol. |

The reaction mixture was agitated for two hours at ambient temperature (20° to 25° C.) while air was introduced using a capillary tube.

After the metal salt had been filtered therefrom, the final reaction mixture was determined using HPLC. The results are reported in Table III below.

The abbreviations used are the same as in Table I.

TABLE III

| TESTS | SOLVENT | RT % HPA | YO % PQI | TR % PQI |
|---|---|---|---|---|
| Example 10 | Chloroform | 5 | 5 | 100 |
| Example 11 | Trifluoroethanol | 21 | 19 | 90 |

EXAMPLE 12

The following reagents were introduced into a 30 cm³ glass reactor:

| (i) CuCl | 1.07 g (10.8 mmol) |
|---|---|
| (ii) Diisopropylethylamine | 5 cm³ |

1 g (5.4 mmol) N-(4-hydroxyphenyl)aniline was introduced by successive additions.

The reaction mixture was agitated for 2 hours at ambient temperature (20° to 25° C.).

After filtration of the metal salt therefrom, the final reaction mixture was determined using HPLC.

The following results were obtained:
RT of HPA = 44%
YO of PQI = 42%
TR of PQI = 96%.

EXAMPLES 13 TO 15

The following reagents were introduced into a tubular reactor provided with fritted glass at the lower end thereof:

| (i) N-(4-Hydroxyphenyl)aniline | 1 g (5 mmol) |
|---|---|
| (ii) Toluene | 25 cm³ |
| (iii) Aqueous 2N soda solution | (amount indicated in Table IV). |

TABLE IV

| TESTS | NaOH (mmol) | RT % HPA | YO % PQI | TR % PQI |
|---|---|---|---|---|
| Example 13 | 25 | 100 | 41 | 41 |
| Example 14 | 5 | 99 | 51 | 52 |
| Example 15 | 0.5 | 21 | 17 | 81 |

EXAMPLES 16 TO 21

The following reagents were introduced into a 30 cm³ glass reactor:

| (i) N-Phenylbenzoquinone-imine | 1.82 g (10 mmol) |
|---|---|
| (ii) 1,3-Dimethylbutylamine | 1 g (10 mmol) |
| (iii) Solvent (indicated in Table V) | 10 cm³. |

This reaction mixture was agitated for 24 hours at 25° C.

The final reaction mixture was determined using HPLC. The following results were obtained.

The abbreviations used are the same as in Table I, plus the following additional abbreviations:

PDBCD = N-phenyl-N'-(1,3-dimethylbutyl)-2,5-cyclohexadiene 1,4-diimine

PMBPD = N-phenyl N'-(1,3-dimethylbutyl)para-phenylenediamine.

TABLE V

| TESTS | SOLVENT | RT % PQI | YO % PDBCD | YO % PMBPD | TR % PDBCD | TR % PMBPD |
|---|---|---|---|---|---|---|
| Example 16 | Ethanol | 83 | 59 | 19 | 63 | 23 |
| Example 17 | 2-Propanol | 65 | 44 | 22 | 68 | 34 |
| Example 18 | Dichloromethane | 22 | 1 | 12 | 4.5 | 54 |
| Example 19 | Isopropyl Ether | 1 | 0.5 | 0.5 | 50 | 50 |
| Example 20 | Toluene | 59 | 9 | 14 | 15 | 24 |
| Example 21 | o-Dichlorobenzene | 45 | 1 | 23 | 2.2 | 51 |

EXAMPLES 22 TO 24

The following reagents were introduced into a 200 cm³ reactor:

| (i) N-phenylbenzoquinone-imine | 4.57 g (25 mmol) |
|---|---|
| (ii) 1,3-Dimethylbutylamine | 2.52 g (25 mmol) |
| (iii) Methanol | 100 cm³. |

The reaction mixture was agitated for 24 hours at the temperature indicated in Table VI.

The final reaction mixture was determined using HPLC.

The following results were obtained:

TABLE VI

| TESTS | Temperature (°C.) | RT % PQI | YO % PDBCD | YO % PMBPD | TR % PDBCD | TR % PMBPD |
|---|---|---|---|---|---|---|
| Example 22 | 25 | 91 | 76.5 | 8 | 84 | 9 |
| Example 23 | 50 | 96 | 86 | 10.5 | 90 | 11 |
| Example 24 | 65 | 96 | 66 | 26 | 69 | 27 |

EXAMPLES 25 TO 27

The following reagents were introduced into a 30 cm³ reactor:

| (i) N-Phenylbenzoquinone-imine | 0.91 g (5 mmol) |
|---|---|
| (ii) 1,3-Dimethylbutylamine | 5 or 25 mmol (see Table VII) |
| (iii) Solvent (indicated in Table VII) | 5 cm³. |

This reaction mixture was agitated for 20 hours at 25° C.

The final reaction mixture was determined using HPLC.

The following results were obtained:

TABLE VII

| TESTS | Solvent | 1,3-Dimethyl butylamine (mmol) | RT % PQI | YO % PDBCD | YO % PMBPD | TR % PDBCD | TR % PMBPD |
| --- | --- | --- | --- | --- | --- | --- | --- |
| Example 25 | Methanol | 5 | 99 | 78 | 21 | 79 | 21 |
| Example 26 | Methanol | 25 | 99 | 17 | 49 | 17 | 49.5 |
| Example 27 | Chloroform | 5 | 57 | 21 | 14 | 37 | 24.5 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

We claim:

1. A process for the preparation of N-phenylbenzoquinone-imine, comprising oxidizing N-(4-hydroxyphenyl)aniline in an at least partially organic liquid reaction medium, in the presence of a basic tertiary amine compound.

2. The process as defined by claim 1, carried out in the presence of a catalytically effective amount of a manganese, copper, cobalt and/or nickel compound.

3. The process as defined by claim 1, said liquid reaction medium being wholly organic.

4. The process as defined by claim 1, said tertiary amine having the formula (I):

wherein $R_1$ and $R_2$, which may be identical or different, are each a linear or branched chain alkyl radical having 1 to 12 carbon atoms or a phenyl radical, and $R_3$ is a linear or branched chain alkyl radical having 1 to 12 carbon atoms, a linear or branched chain alkenyl radical having 2 to 12 carbon atoms, a phenyl radical, a substituted phenyl radical bearing one or two linear or branched chain alkyl radicals having 1 to 4 carbon atoms, a cyclohexyl or cyclopentyl radical, or a benzyl or phenethyl radical.

5. The process as defined by claim 4, wherein the amount of said tertiary amine is at least 1 molar % of the molar amount of said N-(4-hydroxyphenyl)aniline.

6. The process as defined by claim 5, said amount of tertiary amine ranging from 1% to 1,000%.

7. The process as defined by claim 6, said amount of tertiary amine ranging from 50% to 300%.

8. The process as defined by claim 4, wherein the tertiary amine of formula (I) is a non-quaternizable trialkylamine in which $R_1$, $R_2$ and $R_3$ are linear or branched chain alkyl radicals having from 1 to 12 carbon atoms.

9. The process as defined by claim 1, said wholly organic liquid reaction medium comprising an inert solvent.

10. The process as defined by claim 9, said inert solvent comprising an alcohol, ether, ketone, nitrile, N-alkylatedamide, aliphatic or chlorinated aliphatic hydrocarbon, aromatic or chlorinated aromatic hydrocarbon, cycloaliphatic hydrocarbon, ester or sulfoxide.

11. The process as defined by claim 1, said liquid reaction medium comprising a hydro/organic biphasic reaction medium.

12. The process as defined by claim 11, said basic compound comprising an alkali metal hydroxide.

13. The process as defined by claim 12, wherein the molar ratio alkali metal hydroxide/N-(4-hydroxyphenyl)aniline ranges from 5% to 500%.

14. The process as defined by claim 13, said ratio ranging from 10% to 100%.

15. The process as defined by claim 11, said biphasic reaction medium comprising an aliphatic hydrocarbon, chlorinated aliphatic hydrocarbon, aromatic hydrocarbon, chlorinated aromatic hydrocarbon or cycloaliphatic hydrocarbon.

16. The process as defined by claim 12, wherein the water/organic solvent ratio by volume ranges from 0.01 to 100.

17. The process as defined by claim 16, said ratio ranging from 0.1 to 10.

18. The process as defined by claim 2, such metal compound comprising a salt of a mono- or polyfunctional carboxylic acid, or of a halocarboxylic acid, or of a mineral acid, or an oxide or hydroxide.

* * * * *